United States Patent [19]

Adamson, Jr.

[11] Patent Number: 4,556,059
[45] Date of Patent: Dec. 3, 1985

[54] SPRING OPERATED TRACHEOTOME

[76] Inventor: Howard Adamson, Jr., 5813 NW. 18 Ct., Margate, Fla. 33063

[21] Appl. No.: 414,893

[22] Filed: Sep. 3, 1982

[51] Int. Cl.⁴ ............................................. A61B 17/34
[52] U.S. Cl. ............................ 128/305.3; 128/200.26; 128/207.14; 128/324 R; 604/157; 604/161
[58] Field of Search ................. 128/305.3, 305, 329 R, 128/200.26, 314, 315, 329, 330, 207.14; 604/156, 157, 158, 160, 161, 164, 194, 144, 27, 44, 51, 134, 135, 136

[56] References Cited

U.S. PATENT DOCUMENTS

| | | | |
|---|---|---|---|
| 3,556,103 | 1/1971 | Calhoun | 128/200.26 |
| 3,659,610 | 5/1972 | Cimber | 604/157 |
| 3,688,773 | 9/1972 | Weiss | 128/329 |
| 3,797,488 | 3/1974 | Hurschman et al. | 604/136 |
| 3,809,095 | 5/1974 | Cimber | 604/157 |
| 3,817,250 | 6/1974 | Weiss et al. | 604/161 |

OTHER PUBLICATIONS

Toy et al., *A Percutaneous Device*, Surgery, vol. 65, No. 2, Feb. 1969, pp. 384–389.

*Primary Examiner*—Henry J. Recla
*Assistant Examiner*—Karin M. Reichle
*Attorney, Agent, or Firm*—Eugene F. Malin

[57] ABSTRACT

A tracheotome for the automatic mechanical performance of an emergency tracheostomy. An incision into the trachea is made upon release of a power-operated cannula with a cutting blade by a triggering mechanism. The device consists of a powered, hollow cannula with a cutting blade on the frontal edge retained in a hollow, elongated housing. A triggering mechanism releases the cannula to forcefully extend from the housing. The tracheotome is placed adjacent to the throat at an angle and the triggering mechanism is activated. The cutting blade penetrates the tissue and trachea allowing entry of the cannula into the trachea. The cannula and housing provide an immediate temporary channel for air into the trachea and permit a breathing tube to be inserted through them into the trachea. The cannula has a curved portion in its leading edge to direct the insertion of the breathing tube in a downward direction into the trachea to prevent damage to the posterior wall of the trachea. The blade and housing may then be withdrawn over the breathing tube and discarded. The breathing tube is then secured to maintain the air passageway. A non-removeable safety cap is provided to cover the cutting blade before discarding. A rotatably adjustable cap is provided at the mouth of the tracheotome housing to permit control of the extension of the cutting blade from the housing thereby regulating the depth of penetration of the cutting blade into the trachea. A charging handle provides for recocking a spring-operated cutting blade.

9 Claims, 9 Drawing Figures

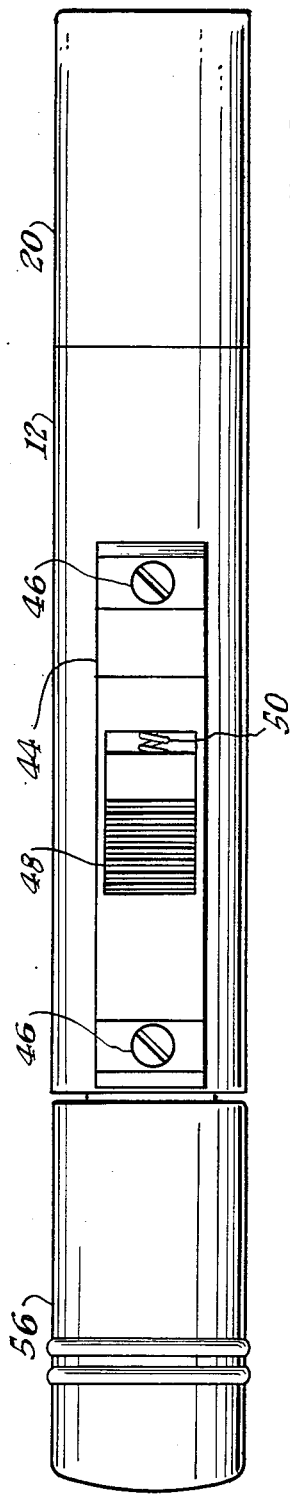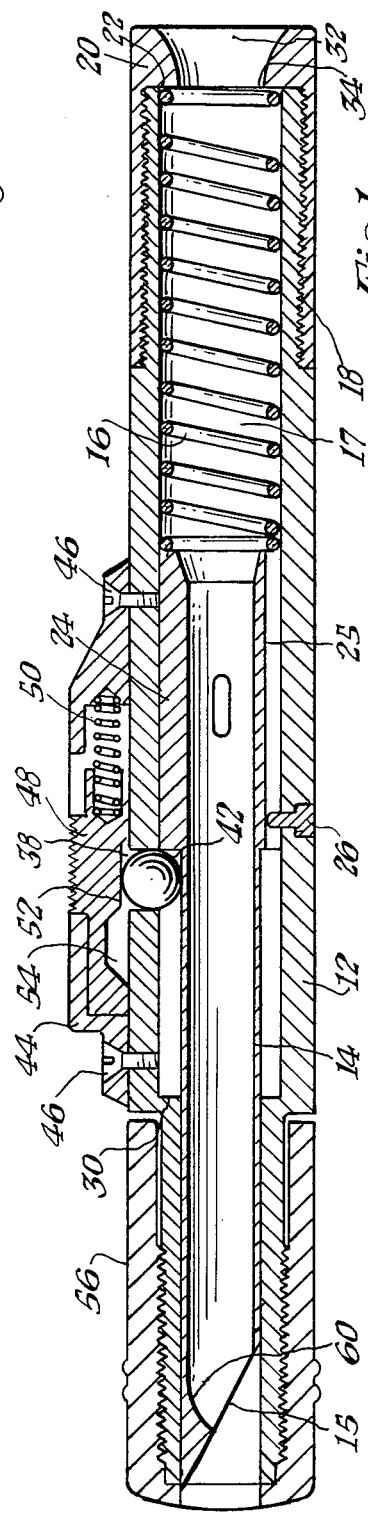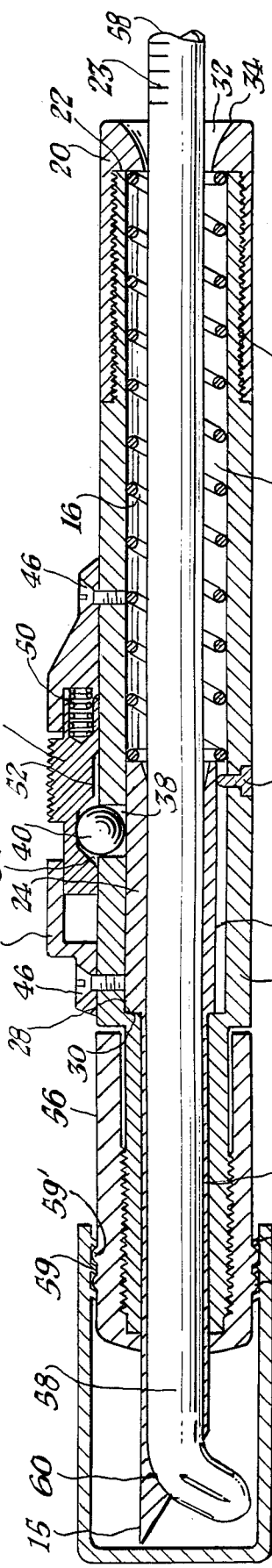

SPRING OPERATED TRACHEOTOME

BACKGROUND OF THE INVENTION

The invention relates to a self-contained, power-operated device for performing a tracheostomy. A tracheostomy is a surgical procedure for creating an opening in the trachea to provide an air passageway without causing traumatic injury to adjacent body tissue and organs. Since the need for a tracheostomy generally arises under primitive, emergency conditions there is insufficient time to transport the patient to a hospital before permanent injury will result from the deprivation of oxygen. There are numerous methods and apparatus pertaining to the introduction of an emergency airway into the trachea but each has its own deficiencies. These methods fail to provide a device which is simple and which can be operated effectively by semi-skilled personnel. The instant invention achieves these goals.

SUMMARY OF THE INVENTION

The present invention relates to a self-contained power-operated tracheotome. The invention is simple in design, simple to operate, effective even in the hands of a semi-skilled operator and is inexpensive to manufacture.

The present invention comprises a propelled hollow, cannula contained within a housing. An adjustable cap is provided to regulate the distance the cannula will extend from the housing upon activation of the spring. A simple triggering mechanism is used to release the cannula which is propelled forward by a power source. A cutting blade on the front edge of the cannula provides an incision into the trachea and allows entry of an extended portion of the cannula while remaining connected to the hollow housing to provide an immediate emergency airway. The internal channel of the housing consists of two portions of differing diameters providing a positive structural stop for the propelled cannula to limit the forward movement of the cannula within the housing and its extension out of the housing. The cannula penetrates the trachea as its blade makes an incision into the trachea to provide an airway. The interior of the housing and the cannula form a temporary air passageway into the trachea upon penetration of the cannula; thereafter a breathing tube is then inserted through the internal channel of the housing and cannula into the trachea. There are markings placed on the breathing tube to indicate the length of the tube being inserted into the tracheotome to determine the length of breathing tube exiting the tracheotome into the trachea. These markings are visible at and compared at the insertion point into the housing. The tracheotome device is then removed over the tube and the tube secured to maintain the air passageway. The device may be recocked for further use or practice. A non-removable protective cap is provided to cover the cutting blade after use for discarding. By use of the present invention a tracheostomy may be performed with surgical precision by a semi-skilled operator. By one single motion, the release of the trigger mechanism, the tracheostomy is swiftly and automatically performed. The self-contained nature of the device will facilitate maintaining it in a sterile condition.

The instant invention is an improvement over existing methods due to its simplicity in design, use and manufacturing. The design is of a pencil-like instrument, which can be operated with one hand and carried in a pocket or purse for instant use. Its use provides for ease, speed and virtually errorless procedures to effect a tracheostomy to provide oxygen into the trachea. In the manufacture of the instant invention it can be made of inexpensive material and would require a very small amount of tooling and engineering prior to production.

Unique features of the instant invention are the control of the exact depth of penetration, insertion of a breathing tube through the device while it is in place in the trachea, knowledge of exact depth of the tube in the trachea due to mark design on the tube and ease in performance of operation and penetration which is most advantageous in saving precious minutes to perform a life-saving procedure. The most unique feature of the instant invention is the complete removal of the device over the inserted breathing tube once the injection has been made to the throat and the tube is in place. The incision is filled completely by the tube so that nothing can enter the incision area. The tube is flexible, and thereby diminishes almost completely the chance of accidental removal of the tube by bumping or striking the tube. In addition, the operator knows exactly the depth of the breathing tube in the trachea by markings on the tube visible at the rear of the housing which can determine depth in inches and centimeters.

It is an object of the subject invention to provide a tracheotome instrument which is uniquely designed for use with ease, speed, and virtually errorless procedure to be insertable into the patient's trachea to provide an emergency airway.

It is another object of the subject invention to provide a tracheotome which may be used by both skilled and semi-skilled personnel in emergency situations.

It is another object of the subject invention to provide a spring-operated tracheotome.

It is another object of the subject invention to to provide a tracheotome in which a straight cutting instrument or trocar may be used to provide ease, speed, and safety during penetration.

It is another object of the subject invention to provide a tracheotome which may be adjusted to regulate the length of exit of the cutting blade and therefore the depth of penetration of the blade into the trachea.

It is another object of the subject invention to provide a spring-operated cutting blade assembly in the tracheotome which may be recocked.

It is another object of the subject invention to provide a trachetome device which may temporarily function as an air passageway.

It is another object of the subject invention to provide a tracheotome through which a breathing tube may be inserted into the trachea.

It is another object of the subject invention to provide a tracheotome which may be removed from the trachea while permitting a previously-inserted breathing tube to be retained in the trachea.

It is another object of the subject invention to provide a tracheotome with a non-removable safety cap to cover the cutting blade after use and during disposal.

These and other objects of the invention, as well as many of the attendant advantages thereof, will become more readily apparent when reference is made to the following description taken in conjunction with the accompanying drawings.

BRIEF DESCRIPTION OF THE DRAWINGS

FIG. 1 shows a side elevational cut-away view of the instant invention.

FIG. 2 shows a top perspective view of the instant invention.

FIG. 3 shows a side elevation cut-away view of the invention in the extended position.

FIG. 7-A shows a front view of the subject breathing tube of the instant invention.

PREFERRED EMBODIMENT OF THE INVENTION

Figure 4:
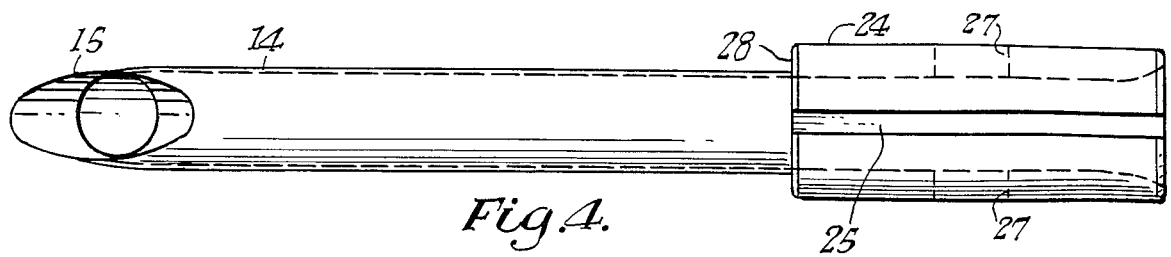
FIG. 4 shows a top perspective view of the subject injector tube of the instant invention.

Referring now to the drawings, and specifically FIG. 1, the instant invention is shown generally at 10 comprising an injector housing 12 containing an injector tube 14 which is propelled by a propelling means such as by injector spring 16. Injector housing 12 is a generally cylindrical, hollow, elongated housing open at both ends forming an internal channel 17. Injector tube 14 is an elongated, hollow cannula with both ends open having a frontal, beveled cutting edge 15 for incision of and insertion into the trachea. Injector tube 14 slidably cooperates within channel 17. On the rear surface of injector tube 14 there is a protruding sleeve 24 with a linear groove 25 for lineal sliding cooperation with guide pin 26 protruding from the wall of injector housing 12 into channel 17. The injector tube 14 may be provided with an additional linear groove on the opposite side of injector tube 14 so that the injector tube 14 could be inserted into injector housing 12 in a position rotated 180 degrees to provide an inverted position for the cutting blade 15. In addition, the trigger mechanism described below may be positioned at any point around the injector housing. The foregoing options will provide for optimum construction of the device to accommodate right-handed and left-handed users and various desired positions for activation by the thumb or forefinger. In any configuration, provision must be made for insuring the breathing tube 58 is inserted downward into the treachea by curved portion 60. The lineal cooperation of the lineal groove 25 and the guide pin 26 prevents rotation of the cutting blade 15 of injector tube 14 when propelled forward by the force of injector spring 16. The forward portion of channel 17 abruptly narrows providing a positive stop allowing the forward portion of injector tube 14 to proceed forward in response to the force of injector spring 16 until the leading edge 28 of sleeve 24 impinges against the protruding wall 30 of injector housing 12. Portion 18 of the rear, outer surface of injector housing 12 is threaded for screw-on cooperation. Injector spring cap 20 is an elongated, hollow cylinder with two open ends and provides for screw-on cooperation with portion 18 to provide an inner, circular rim protrusion 22 upon which one end of injector spring 16 will impinge to prevent rearward movement. Aperture 34 tapers outward and defines a channel 32 which is in axial communication with channel 17 thereby providing a passageway for air through channels 17 and 32. The outward taper of aperature 34 facilitates the insertion of a breathing tube 58 into channel 32. Injector tube 14 is slideably inserted with the sleeve 24 rearward through injector housing 12 engaging guide pin 26 with the injector tube groove 25 to impinge against forward spring edge 36 and compress the injector spring 16 against rim protrusion 22. The outer surface of injector housing 12 has aperture 38 which allows the placement of a ball bearing 40 so that the lower portion 42 of the spherical ball bearing 40 is in contact and impinges against leading edge 28 of sleeve 24 after compression of injector spring 16. The vertical walls of aperture 38 prevent horizontal forward or rearward movement of ball bearing 40 as a result of the impinging force of leading edge 28. The top edge of the leading edge 28 is situated at a sufficient distance below the center of gravity of ball bearing 40 so that the contact of leading edge 28 on the curvilinear surface of ball bearing 40 causes an upward force on ball bearing 40 to propel it upward out of aperture 38 as a result of the force of injector spring 16 on injector tube 14. A trigger housing 44 is attached to the outer surface of the injector housing 12 by such fasteners as screw 46. Trigger housing 44 encloses a release mechanism 48 held in juxtaposition over the aperture 38 by a trigger spring 50. A retainer portion 52 of release mechanism impinges against the top of the ball bearing to resist upward movement and to retain it in aperture 38. Upon rearward slideable movement of release mechanism 48 to compress trigger spring 50 a cavity portion 54 is exposed to aperture 38 which allows upward movement of ball bearing 40 beyond impinging contact with leading edge 28 releasing injector tube 14 to proceed forward. As ball bearing 40 is forced upward into cavity portion 54 the injector tube is propelled forward by the horizontal, lineal force of compressed injector spring 16 along channel 17 to protrude out of injector housing 12 until leading edge 28 impinges against protruding wall 30.

In FIG. 3 is shown the extended position of the injector tube 14. While injector tube 14 is extended forward, ball bearing 40 is housed in cavity portion 54. The distance which injector tube 14 will extend out of injector housing 12 is regulated by blade cap 56 which attaches to the frontal end of injector housing by an adjustable means such as threaded cooperation shown in FIGS. 2 and 3. A protective cap 57 is inserted over blade cap 56 when cutting blade 15 is in the extended position after use to prevent an inadvertent cutting. Protective cap 57 is non-removable by virtue of binding cooperation between protrusions 59 and 59'. In this embodiment, blade cap 56 may be extended by rotating it to utilize the threaded connection to adjust the relative position of the cap 56 and housing 12 thereby increasing the length of channel 17 and reducing the portion of injector tube 14 which may be inserted into the trachea. This adjustment allows the device to be adapted for use with either obese adults, or normal children and even infants. The reduction in length of the protrusion of the injector tube 14 into the trachea compensates for the varying diameters of trachea of the various age groups and prevents injury which may be caused by the injector tubes cutting the posterior tracheal membrane which is very soft tissue. Upon insertion of the injector tube 14 into the trachea 68 (shown in FIG. 8) an emergency airway for the trachea 68 is established by air passing through aperture 34 into channel 32 through channel 17 into the hollow passageway of injector tube 14 and into the trachea. Having established this emergency airway by use of the instant invention, a breather tube 58 is then passed through aperture 34 and the above described air passages into the trachea 68 as shown in FIG. 3. Breather tube 58 has graduated markings 23 to determine the length of the breather tube protruding from injector tube 14 into the trachea and FIG. 8. After breather tube 58 is inserted through device 10 into the trachea 68 the device 10 is then removed by extracting it from the trachea and slideably removing it over breather tube 58. The breather, tube 58 is then secured to maintain the air passageway.

Figure 5:
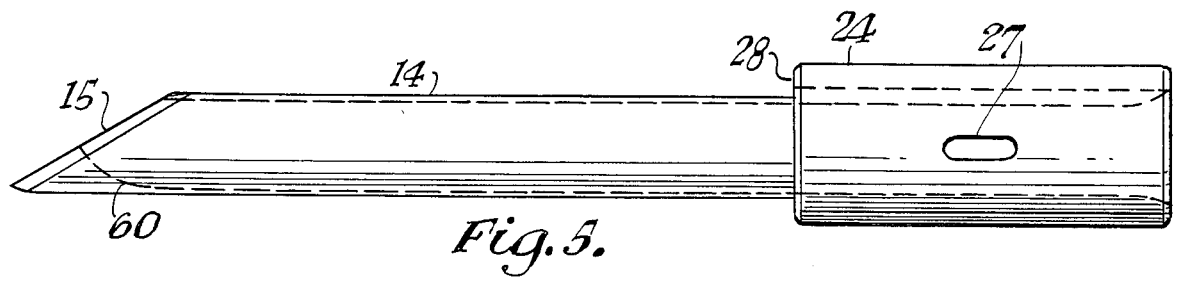
FIG. 5 shows a side perspective view of the subject injector tube of the instant invention.
Figure 6:
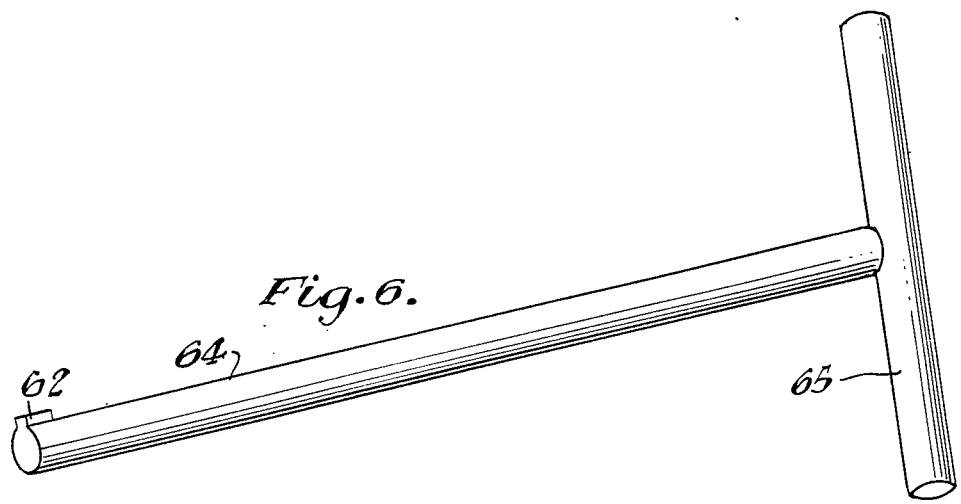
FIG. 6 shows a perspective view of the cocking tool of the perspective invention.

FIGS. 4 and 5 show the injector tube 14 with sleeve 24 and linear groove 25. Leading edge 28 of sleeve 24 provides for a cocked position by impingement against ball bearing 40 (as shown in FIG. 1), when the injector spring 16 is compressed. In the injector tube 14, extended position leading edge 28 impinges against protruding wall 30 and is held in position to provide an emergency airway by the force of injector spring 16 (as shown in FIG. 3). Injector tube 14 has a beveled cutting blade 15 for providing a smooth incision through the skin, facia and trachea wall. Adjacent to the cutting blade 15 the passageway of injector tube 14 is provided a curved portion 60 to direct the breather tube 58 downward into the trachea to prevent insertion backward against the soft posterior tracheral tissue resulting in injury to the tissue or clogging of the opening of the breather tube 58. Locking port 27 (FIGS. 1, 4 and 5) is one of two such apertures in sleeve 24. Protrusion 62 on shaft 63 of locking tool 64 is inserted into port 27 to provide rearward displacement of injector tube 14 compressing injector spring 16 to recock the device 10. In addition, injector tube 14 may be provided with an internal protruding ridge or indention to provide for engagement by protrusion 12. Tool 64 is inserted through aperture 34, channels 32 and 17 to engage the port 27 or other engaging structure when injector tube 14 is in the extended position (FIG. 3). Injector tube 14 is displaced rearward against injector spring 16 by pulling on handle 65 until ball bearing 40 descends from cavity position 54 to impinge against leading edge 28. Trigger spring 50 compels release mechanism 48 forward so that portion 52 is positioned above ball bearing 40 to prevent its upward movement. The device 10 is now recocked and prepared to be reused.

Figure 7:
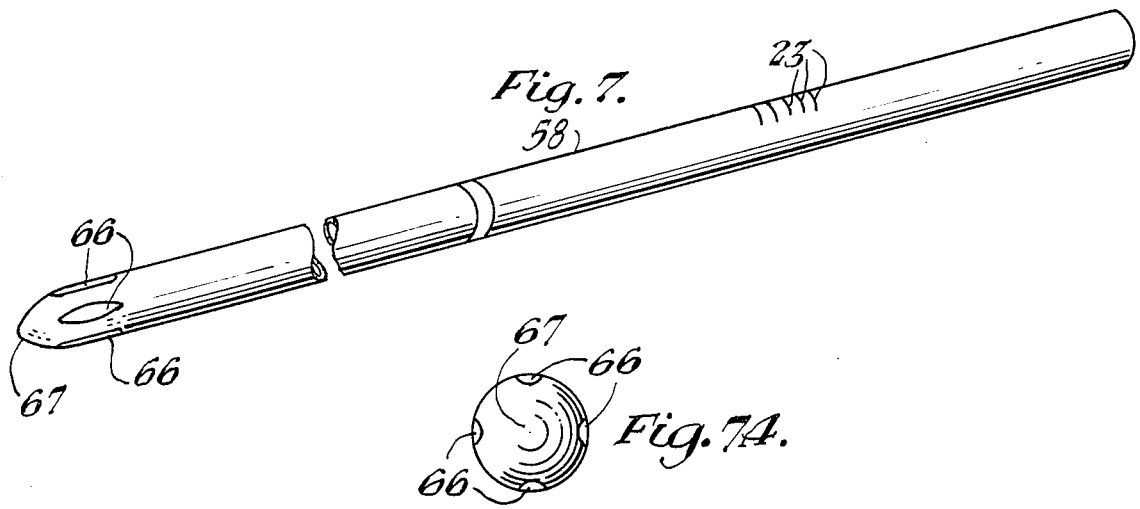
FIG. 7 shows a perspective view of the subject breathing tube of the instant invention.
Figure 7A:
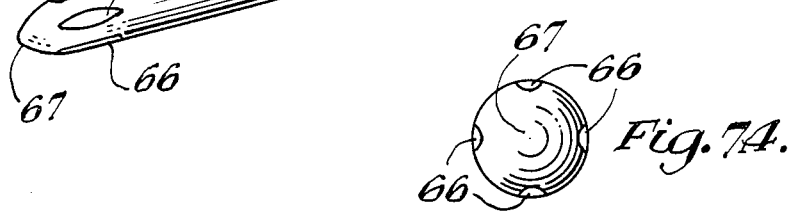

FIGS. 7 and 7A show the tip 67 of the breather tube 58 with a plurality of breathing aperture 66 situated on the surface of tube 58 and disposed coaxially with the inner airway of tube 58. The closed tip 67 of tube 58 provides no edges to cut or bruise the posterior tracheal tissue upon insertion of breather tube 58 through device 10 into the trachea. Aperture 66 provides a displaced air passage to prevent clogging by contact with the posterior tracheal tissue.

FIG. 2 shows a top view of device 10 demonstrating the location of trigger housing 44 held in place by screw 46 and encloses release mechanism 48.

Figure 8:
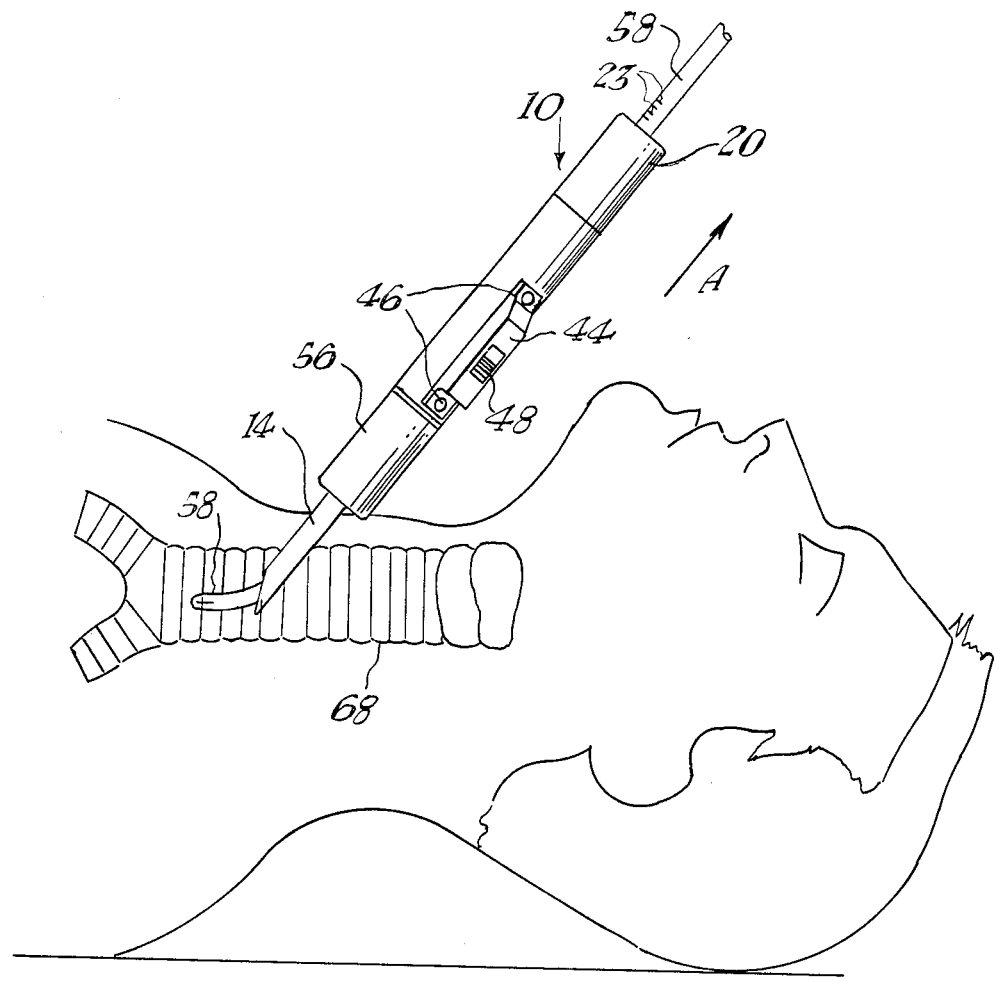
FIG. 8 provides a partial cut-away view of the trachea to demonstrate the insertion of the tracheotome into the trachea.

FIG. 8 demonstrates the utilization of the instant invention in penetrating the trachea 68 with injector tube 14 and subsequent insertion of breathing tube 58. The markings 23 provide an indication of the depth of insertion of breathing tube 58. Trigger housing 44 is shown placed on the left side of the device which would accommodate thumb activation by a right-hand user or forefinger operation by a left-hand user. The device 10 may be removed after implacement of the breathing tube 58 by removal over tube 58 in direction A. Housing 12 is clearly marked "top" to show exact blade position for entrance into trachea and guidance of the breathing tube into the trachea.

While the present invention has been described with particularity, it should be understood that various modifications and alterations may be made therein without departing from the spirit and scope of the invention set forth in the appended claims.

What we claim is:

1. A tracheotome for performing a tracheostomy and passing a breathing tube into the trachea of a patient comprising:

elongated, open-ended and hollow housing means;
   elongated, open-ended and hollow injector means with trachea puncturing means at one open end thereof and forming an internal channel, said injector means being slidably positioned within said housing means, said housing means and said injector means channel adapted for receiving the breathing tube therethrough and said injector means channel including a portion which is curved with respect to the longitudinal axis of said injector means located adjacent the one open end of said injector means and which is adapted to direct said received breathing tube into said trachea;
   means for propelling the one open end of said injector means out of said housing means into the trachea of a patient; and
   means for normally retaining the one open end of said injector means within said housing means and for selectively controlling propulsion of said injector means into the trachea by said propelling means, said means for normally retaining and selectively controlling including trigger means.

2. The invention according to claim 1 wherein said means for propelling includes releaseable spring means.

3. A tracheotome providing for the spring-powered insertion of a breathing channel into the trachea of a patient and the insertion of a breathing tube through the breathing channel into the trachea and for removal of the tracheotome over the inserted breathing tube, comprising:

a housing, an elongated, hollow cannula, compressible spring means for impinging contact with said housing and said cannula and triggering means connected to said cannula and said housing;
   said housing having a linear, elongated channel therethrough which is open at both ends thereof and adapted to slidably accommodate said cannula, said channel including a positive structural stop means for impinging contact with said cannula, said housing having adjustable blade end cap means at one open end for defining an exit for said cannula from said housing, said housing having spring cap means at the other open end for defining an entrance for air and the breathing tube into said housing;
   said cannula being slidably contained within said channel and having two opposite open ends and forming a breathing channel adapted to slidably accomodate the breathing tube and providing a pathway for air, said cannula having an oblique cutting edge with respect to the longitudinal axis of said cannula at the one open end adjacent the one open end of said housing and said cannula channel having a portion which is curved with respect to the longitudinal axis of said cannula at said one open end adapted for bending the breathing tube, thereby directing it into the trachea when said breathing tube is inserted into the trachea through said cannula said spring means being normally held in a compressed position by said triggering means between the other open end of said cannula and said spring cap means and being selectively released from the compressed position by said triggering means allowing powered insertion of the one open end of said cannula thereby into the trachea, said spring means defining a passageway for air and the breathing tube from said spring cap means to the other open end of said cannula; and said triggering means including a two-position release switch means and movable ball means for impinging with said cannula.

4. A tracheotome for performing a tracheostomy, and passing a breathing tube into a patient, comprising:

injector means for defining a passage for air and for insertion therethrough of the breathing tube; and housing means for retaining, triggering and propelling said injector means for adjustable insertion of said injector means into said trachea;

said injector means comprising an elongated hollow cannula with two opposite open ends forming an internal channel which defines a passage for air and for insertion therethrough of the breathing tube, one open end of said cannula having an oblique edge with respect to the longitudinal axis of said hollow cannula defining a cutting blade;

the internal channel of said cannula having a portion which is curved with respect to the longitudinal axis of said hollow cannula adjacent to said oblique edge adapted to direct the breathing tube when inserted therethrough into the trachea of a patient;

said cannula comprising a rear end portion adjacent the other open end of said hollow cannula and a front end portion adjacent the one open end of said hollow cannula, said rear end portion having a greater diameter than a front end portion of said cannula, said cannula defining an outer annular protruding shoulder at the intersection of said front and rear end portions;

said housing means comprising an elongated hollow housing with two opposite open ends forming an internal channel adapted to slidably receive said injector means therein and providing a passage through which air and the breathing tube may pass to said injector means received therein, said channel comprising a rear portion adjacent one open end of said housing and a front portion adjacent the other open end of said housing, said front portion having a smaller diameter than a rear portion of said channel;

said front portion adapted to slidably accomodate said front end portion of said injector means, said rear portion adapted to slidably accomodate said rear end portion of said injector means, said channel defining a protruding structural stop at the intersection of said rear channel portion and said front channel portion adapted to impinge with the protruding shoulder of said injector means;

said housing having blade end cap means for defining an exit for said injector means from said housing adjustably connected to the other open end of said housing by thread means, said housing having injector spring cap means for defining an entrance for air and the breathing tube into the housing connected to the one open end of said housing by thread means, said front end portion of said injector means being substantially longer than the front portion of said housing means, said rear end portion of said injector means being substantially shorter than the rear portion of said housing, said injector means positioned in said internal channel of said housing with said front end portion of said injector means in slidable cooperation with said front channel portion of said housing, said rear end portion in slidable cooperation with said rear channel portion of said housing and said protruding shoulder in slidable cooperation with said rear channel portion of said housing;

said housing means further including triggering means and propelling means, said triggering means connected to said injector means for normally retaining said injection means within said housing and for selectively triggering propulsion of said injector means by said propelling means; and said propelling means connected to said injector means for providing upon the selective triggering of said triggering means a propelling force to said injector means to cause said injector means to slide forward within said internal channel until the front end portion forcibly extends from the other open end of said housing means and adjustable distance to cut and penetrate into said trachea and said protruding shoulder impinges against said structural stop.

5. A tracheotome as recited in claim 3 wherein:

said propelling means comprises a linear helical spring having first and second ends retained in the rear channel portion of said housing with said first and second ends impinging against said spring cap means and said cannula, respectively, said spring defining a passageway for air and the breathing tube from said spring cap means to said other open end of said cannula, said spring being normally compressed between said cannula and said spring cap means when said cannula is normally retained by said triggering means, and said spring being released from the normally compressed position and said cannula being propelled forward within said internal channel by said spring upon selective triggering of said cannula by said triggering means.

6. A tracheotome as recited in claim 5, wherein:

said triggering means is a movable, impinging ball bearing apparatus, said apparatus comprising a trigger housing, a release mechanism, a trigger spring means, and a ball bearing, said housing means including an aperture through the side wall thereof into the internal channel thereof, said aperture located in the rear channel portion and adapted to slidably receive said ball bearing, said ball bearing positioned within said aperture, said trigger housing defining an open sided cavity and being connected to the outer surface of said housing means with said cavity overlying said aperture by a plurality of fasteners, said release mechanism having one side surface with a recessed portion and a level portion adjacent thereto, said release mechanism slidably positioned within the cavity of said trigger housing with the one side surface overlying said aperture, said trigger spring means located between said level portion and said trigger housing for providing normally biased retention of said level portion over said aperture and said ball bearing, said trigger housing further including means for allowing manual release of the biased retention of said level portion and positioning of the recessed portion over the aperture and the ball bearing, whereby in the normally biased position, said ball bearing is restrained by walls of said aperture and said level portion of said release mechanism in impinging contact with the front edge of said protruding shoulder of said cannula thereby retaining said cannula within said housing, and in the release position, the biased retention of said level portion over said aperture is overcome by said manual release means and said recessed portion is positioned over the aperture and receives said ball bearing to release said cannula from impinging contact and to allow propulsion of said cannula by said propelling means into the trachea.

7. A tracheotome as recited in claim 6 further including:
a breathing tube adapted for slidable insertion through said spring cap means, said spring, said housing means and said cannula into said trachea, said tracheotome adapted for slidable removal over the inserted breathing tube, and said breathing tube having depth insertion marks.

8. A tracheotome as recited in claim 7 further including cocking port means positioned in said injector means; and
cocking hand tool means adapted for slidable insertion into said housing means for returning said injector means to its normally retained position within said housing means from its extended position after removal thereof over the inserted breathing tube, and said cocking tool means including protrusion means for insertion into said cocking port means.

9. A tracheotome as recited in claim 8, further including:
protective cap means removably positioned over said blade end cap means for covering the front end portion of said cannula extending out of said housing means after removal of the tracheotome over the inserted breathing tube.

* * * * *